US007998222B2

(12) United States Patent  (10) Patent No.: US 7,998,222 B2
Morrissey et al.  (45) Date of Patent: Aug. 16, 2011

(54) COSMETIC COMPOSITIONS COMPRISING A POLYMER AND A COLORANT

(75) Inventors: Christopher Todd Morrissey, Mason, OH (US); David Michael Piatt, Cincinnati, OH (US); Curtis Bobby Motley, West Chester, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 12/906,533

(22) Filed: Oct. 18, 2010

(65) Prior Publication Data

US 2011/0033401 A1  Feb. 10, 2011

Related U.S. Application Data

(63) Continuation of application No. 10/840,833, filed on May 7, 2004, now Pat. No. 7,837,742.

(60) Provisional application No. 60/471,594, filed on May 19, 2003.

(51) Int. Cl.
*A61Q 5/10* (2006.01)
*A61K 8/00* (2006.01)

(52) U.S. Cl. .......... 8/405; 8/455; 8/552; 8/557; 8/637.1; 132/202; 132/208; 424/70.1

(58) Field of Classification Search ............. 8/405, 455, 8/552, 554, 557, 637.1; 132/202, 208; 424/70.1
See application file for complete search history.

(56) References Cited

U.S. PATENT DOCUMENTS

| | | |
|---|---|---|
| 2,798,053 A | 7/1957 | Brown |
| 3,196,079 A | 7/1965 | Blaustein |
| 3,449,319 A | 6/1969 | Kuhn |
| 366,690 A | 5/1972 | Bann |
| 3,912,808 A | 10/1975 | Sokol |
| 3,913,834 A | 10/1975 | Supper |
| 3,958,581 A | 5/1976 | Abegg |
| 3,962,418 A | 6/1976 | Birkofer |
| 3,986,825 A | 10/1976 | Sokol |
| 4,027,008 A | 5/1977 | Sokol |
| 4,228,259 A | 10/1980 | Kalopissis |
| 4,268,499 A | 5/1981 | Keil |
| 4,438,140 A | 3/1984 | Guillon |
| 4,492,686 A | 1/1985 | Guillon |
| 4,509,949 A | 4/1985 | Huang |
| 4,559,057 A | 12/1985 | Bogaty |
| 4,588,617 A | 5/1986 | Oka |
| 4,599,379 A | 7/1986 | Flesher |
| 4,602,886 A | 7/1986 | Smit |
| 4,628,078 A | 12/1986 | Glover |
| 4,650,672 A | 3/1987 | Yagita |
| 4,665,107 A | 5/1987 | Micale |
| 4,752,528 A | 6/1988 | Oka |
| 4,756,906 A | 7/1988 | Sweeny |
| 4,801,445 A | 1/1989 | Fukui |
| 4,818,614 A | 4/1989 | Fukui |
| 4,830,485 A | 5/1989 | Penney |
| 4,835,206 A | 5/1989 | Farrar |
| 4,849,484 A | 7/1989 | Heard |
| 4,879,174 A | 11/1989 | Marabella |
| 4,879,175 A | 11/1989 | Marabella |
| 4,880,617 A | 11/1989 | Abrutyn |
| 4,882,225 A | 11/1989 | Fukui |
| 4,919,922 A | 4/1990 | Miyoshi |
| 4,943,430 A | 7/1990 | Hefford |
| 4,976,953 A | 12/1990 | Orr |
| 5,087,445 A | 2/1992 | Haffey |
| 5,087,447 A | 2/1992 | Racz |
| 5,100,660 A | 3/1992 | Hawe |
| 5,116,410 A | 5/1992 | Miller |
| 5,143,722 A | 9/1992 | Hollenberg |
| 5,184,148 A | 2/1993 | Suga |
| 5,330,747 A | 7/1994 | Krzysik |
| 5,368,639 A | 11/1994 | Hasegawa |
| 5,458,681 A | 10/1995 | Hasegawa |
| 5,505,937 A | 4/1996 | Castrogiovanni |
| 5,556,617 A | 9/1996 | Ribier |
| 5,631,309 A | 5/1997 | Yanagi |
| 5,654,362 A | 8/1997 | Schulz |
| 5,681,852 A | 10/1997 | Bissett |
| 5,686,082 A | 11/1997 | N'Guyen |
| 5,686,084 A | 11/1997 | Wenke |
| 5,686,367 A | 11/1997 | Hayashi |
| 5,772,696 A | 6/1998 | Sujeeth |
| 5,827,330 A | 10/1998 | Wenke |
| 5,880,210 A | 3/1999 | Schulz |

(Continued)

FOREIGN PATENT DOCUMENTS

| | | |
|---|---|---|
| DE | 1913569 | 10/1969 |
| DE | 03246747 A1 | 6/1984 |
| DE | 10056266 A1 | 5/2002 |
| DE | 10101206 A1 | 7/2002 |
| EP | 228868 | 1/1988 |
| EP | 225799 B1 | 4/1990 |
| EP | 306331 | 6/1990 |

(Continued)

OTHER PUBLICATIONS

Fox, C., "Color in Cosmetics", Cosmetics & Toiletries, vol. 111, No. 3, pp. 35-53 Mar. 1996.
Fox, C., "Skin and Skin Care", Cosmetics & Toiletries, vol. 112, No. 2, pp. 21-25 (Feb. 1997).
Fox, C., "Skin and Skin Care", Cosmetics & Toiletries, vol. 116, No. 7, pp. 28 & 30-33 (Jul. 2001).
Barbeito, C., et al., "The Condition of Colour", Soap Perfum. Cosmet., vol. 65, No. 11, pp. 31-32 (1992).

(Continued)

*Primary Examiner* — Eisa B Elhilo
(74) *Attorney, Agent, or Firm* — John G. Powell; Megan C. Hymore

(57) ABSTRACT

A cosmetic composition suitable for use on mammalian skin, hair, and nails. These compositions contain a polymer and a colorant. The polymer of the composition mitigates staining caused by the colorant, and the polymer and colorant are opposite in charge. The present invention is also directed to methods of mitigating skin staining through using the cosmetic compositions.

15 Claims, No Drawings

U.S. PATENT DOCUMENTS

| | | | |
|---|---|---|---|
| 5,935,826 | A | 8/1999 | Blue |
| 5,948,420 | A | 9/1999 | Ferhut |
| 5,993,831 | A | 11/1999 | Ribier |
| 5,997,887 | A | 12/1999 | Ha |
| 6,019,962 | A | 2/2000 | Rabe |
| 6,040,359 | A | 3/2000 | Santini |
| 6,060,084 | A | 5/2000 | Sullivan |
| 6,060,547 | A | 5/2000 | Canter |
| 6,071,503 | A | 6/2000 | Drechsler |
| 6,074,654 | A | 6/2000 | Drechsler |
| 6,086,917 | A | 7/2000 | Trubiano |
| 6,114,156 | A | 9/2000 | McDaniel |
| 6,114,411 | A | 9/2000 | Nakamura |
| 6,123,951 | A | 9/2000 | Gueret |
| 6,139,823 | A | 10/2000 | Drechsler |
| 6,231,622 | B1 * | 5/2001 | Chassot et al. .............. 8/405 |
| 6,290,936 | B1 | 9/2001 | Ross |
| 6,340,466 | B1 | 1/2002 | Drechsler |
| 6,368,662 | B1 | 4/2002 | McDaniel |
| 6,406,683 | B1 | 6/2002 | Drechsler |
| 6,471,951 | B1 | 10/2002 | Nardolillo |
| 6,482,917 | B1 | 11/2002 | Hildebrandt |
| 6,503,495 | B1 | 1/2003 | Alwattari |
| 6,533,857 | B1 | 3/2003 | Schmid |
| 6,555,097 | B1 | 4/2003 | Rabe |
| 6,620,410 | B1 | 9/2003 | Cho |
| 6,890,653 | B2 | 5/2005 | Wulff |
| 2001/0044493 | A1 | 11/2001 | VanDahm |
| 2002/0035197 | A1 | 3/2002 | VanDahm |
| 2002/0058596 | A1 | 5/2002 | Maubru |
| 2002/0064541 | A1 | 5/2002 | Lapidot |
| 2002/0122780 | A1 | 9/2002 | McManus |
| 2003/0003065 | A1 | 1/2003 | Kalla |
| 2003/0026815 | A1 * | 2/2003 | Scott et al. .............. 424/401 |
| 2003/0095941 | A1 | 5/2003 | Anderson |
| 2003/0118530 | A1 | 6/2003 | O'Brien |
| 2003/0180235 | A1 | 9/2003 | Grisoni |
| 2004/0232575 | A1 | 11/2004 | Wulff |

FOREIGN PATENT DOCUMENTS

| | | |
|---|---|---|
| EP | 212870 | 4/1992 |
| EP | 238225 | 7/1992 |
| EP | 557115 A | 8/1993 |
| EP | 0371551 B1 | 10/1993 |
| EP | 581652 | 2/1994 |
| EP | 232001 | 3/1994 |
| EP | 522916 | 9/1997 |
| EP | 767225 A2 | 4/2003 |
| EP | 1048285 | 10/2003 |
| EP | 922449 | 1/2007 |
| GB | 2107186 | 12/1984 |
| JP | 49057538 | 6/1974 |
| JP | 50049169 | 5/1975 |
| JP | 54063132 A2 | 5/1979 |
| JP | 58180421 A2 | 10/1983 |
| JP | 59076009 | 4/1984 |
| JP | 59128322 | 7/1984 |
| JP | 60045511 A | 3/1985 |
| JP | 60064922 A2 | 4/1985 |
| JP | 61047410 | 3/1986 |
| JP | 61083109 | 4/1986 |
| JP | 61166827 | 7/1986 |
| JP | 62209011 | 9/1987 |
| JP | 62234541 | 10/1987 |
| JP | 62254833 | 11/1987 |
| JP | 63060914 | 3/1988 |
| JP | 63090573 A2 | 4/1988 |
| JP | 63171678 | 7/1988 |
| JP | 63179972 | 7/1988 |
| JP | 63196505 | 8/1988 |
| JP | 63202671 | 8/1988 |
| JP | 200003404 | 1/1990 |
| JP | 3293028 | 12/1991 |
| JP | 4001118 | 1/1992 |
| JP | 04005217 A2 | 1/1992 |
| JP | 04149277 A | 5/1992 |
| JP | 05032536 A | 2/1993 |
| JP | 5339518 | 12/1993 |
| JP | 10017437 | 1/1998 |
| JP | 10059818 | 3/1998 |
| JP | 10101530 | 4/1998 |
| JP | 1998245319 A | 9/1998 |
| JP | 11197494 | 7/1999 |
| JP | 11209238 | 8/1999 |
| JP | 1999335239 A | 12/1999 |
| JP | 2000034303 | 2/2000 |
| JP | 2000344624 A | 12/2000 |
| JP | 20011172140 A | 6/2001 |
| JP | 20011206839 A | 7/2001 |
| JP | 2001226240 A | 8/2001 |
| JP | 20011213726 A | 8/2001 |
| JP | 2002029946 A | 1/2002 |
| JP | 2002087944 A2 | 3/2002 |
| KR | 100153371 B1 | 3/1998 |
| SU | 1176289 A | 8/1985 |
| WO | WO9305753 | 4/1993 |
| WO | WO9410968 A1 | 5/1994 |
| WO | WO9633689 | 10/1996 |
| WO | WO9717058 | 5/1997 |
| WO | WO9818867 | 5/1998 |
| WO | WO9818431 | 7/1998 |
| WO | WO98/36032 | 8/1998 |
| WO | WO9850002 | 11/1998 |
| WO | WO9943426 | 9/1999 |
| WO | WO0009652 A2 | 2/2000 |
| WO | WO0109257 A1 | 2/2001 |
| WO | WO0051553 | 8/2001 |
| WO | WO0178664 A1 | 10/2001 |
| WO | WO0178671 A2 | 10/2001 |
| WO | WO0234220 A2 | 5/2002 |
| WO | WO0283073 A2 | 10/2002 |
| WO | WO03015910 | 2/2003 |
| WO | WO02102350 | 3/2003 |

OTHER PUBLICATIONS

PCT International Search Report, International Application No. PCT/US2004/015375 of May 14, 2004.

PCT Publication No. 95/34280, 95/07432, 95/23780 (1995).

* cited by examiner

COSMETIC COMPOSITIONS COMPRISING A POLYMER AND A COLORANT

CROSS REFERENCE OF RELATED APPLICATION(S)

This application is a continuation of U.S. application Ser. No. 10/840,833, filed on May 7, 2004, now U.S. Pat. No. 7,837,742 which claims the benefit of Provisional Application Ser. No. 60/471,594, filed May 19, 2003.

FIELD OF INVENTION

The present invention relates to cosmetic compositions suitable for use on mammalian skin, hair, and nails. These compositions contain a polymer and a colorant. The polymer of the composition mitigates staining caused by the colorant, and the polymer and colorant are opposite in charge. The present invention is also directed to methods of mitigating skin staining through using the cosmetic compositions.

BACKGROUND

Colorants are used to provide permanent, semi-permanent, and temporary color to personal care products for the hair and skin. Often, the colorants used are dyes, which can stain or color the desired substrate. In many applications, staining is undesirable which limits the use of dyes. Therefore, dyes are typically converted to lakes which render the dye mostly insoluble. However, in the presence of water or another suitable solvent, some of the dye is leached from the lake leaving the same staining potential. Other strategies have been used to immobilize colorants such as encapsulation, but none of these strategies are entirely effective.

Permanent and semi permanent hair dyes use gloves and other means to avoid staining the skin. These permanent and semi permanent dyes will provide a lasting color to the skin. This is in contrast to many dyes, which provide only a temporary or transient staining. However, this transient stain is still perceivable by consumers. Thus, there still exists a need to reduce or mitigate the temporary staining such that the consumer can wipe the product off their skin, hair, and nails and leave no noticeable stain prior to washing.

SUMMARY OF THE INVENTION

The present invention relates to a cosmetic composition containing a polymer and a colorant, where the polymer mitigates staining on keratinaceous substances including skin, hair, and nails caused by the colorant, and the polymer and colorant are opposite in charge. Preferably, the polymer is a cationic polymer and the colorant is an anionic colorant selected from the group consisting of pigments, encapsulated dyes, lakes, and mixtures thereof.

In another embodiment of the invention, the cosmetic composition has a spectrophotometric curve, wherein a first derivative of the spectrophotometric curve comprises: a) a maximum peak in the region of from about 430 nm to about 520 nm occurs at a wavelength not greater than about 480 nm; b) a maximum peak in the region of from about 420 nm to about 650 nm occurs at a wavelength of from about 570 nm to about 630 nm; and c) a minimum valley in the region of from about 520 nm to about 580 nm has $\Delta\% R/\Delta\lambda$ of less than or equal to about 0.03, wherein R is reflectance and $\lambda$ is wavelength, and wherein the cosmetic composition comprises a mixture of at least two colorants, wherein a first derivative of the spectrophotometric curve of each of the individual colorants does not exhibit (a), (b) and (c).

In another embodiment, the invention is directed to methods of mitigating staining of skin, hair, and nails through using the cosmetic compositions.

DETAILED DESCRIPTION OF THE INVENTION

As used herein, "cosmetic composition" means any color cosmetic, hair, nail, or skin care product. "Cosmetic compositions" include, but are not limited to products that leave color on the face, including foundation, blacks and browns, i.e., mascara, concealers, eye liners, brow colors, eye shadows, blushers, lip sticks, lip balms, face powders, solid emulsion compact, and so forth. The term "foundation" refers to liquid, creme, mousse, pancake, compact, concealer or like product created or reintroduced by cosmetic companies to even out the overall coloring of the skin.

As used herein, "transient stain" is a stain that does not rub off, but can be removed by water alone or the combination of soap and water, or will fade in less than about 24 hours.

As used herein, both "spectrophotometric curve" and "spectral curve" refer generally to a plotted curve displaying an ordinate value of relative reflectance versus an abscissa value of wavelength of light, typically within the visual range of about 400-700 nm.

Herein, "comprising" means that other steps and other ingredients which do not affect the end result can be added. This term encompasses the terms "consisting of" and "consisting essentially of". The products, compositions and methods/processes of the present invention can comprise, consist of, and consist essentially of the essential elements and limitations of the invention described herein, as well as any of the additional or optional ingredients, components, steps, or limitations described herein.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt. %" herein.

All measurements made are at 25° C., unless otherwise designated.

A. Polymer

The composition of the present invention includes a polymer. The polymer is included to mitigate skin staining caused by colorants in the composition. The polymer of the composition includes cationic polymers, anionic polymers, nonionic polymers, amphiphilic polymers, or mixtures thereof, so long as a portion of the polymer and colorant are opposite in charge. Such polymers should be physically and chemically compatible with the essential components described herein, or should not otherwise unduly impair product stability, aesthetics or performance.

Suitable polymers for use in the composition herein include those which are known for use in cosmetic compositions or other personal care compositions. The concentration of the polymer generally ranges from about 0.001% to about 50%, preferably from about 0.1% to about 15%, more preferably from about 0.2% to about 5%, even more preferably from about 0.5% to about 2%, by weight of the composition.

Preferred polymers suitable for use in the compositions are cationic polymers. In general, cationic polymer denotes any polymer containing cationic groups and/or groups which may be ionized into cationic groups. The cationic polymers are selected from those that contain units comprising primary, secondary, tertiary and/or quaternary amine groups which may either form part of the main polymer chain or may be side substituents linked to the main chain. Suitable cationic polymers can be found in the International Cosmetic Ingredient Dictionary (7th ed. 1997). Preferably, the organic cationic polymer contains cationic nitrogen-containing moieties such as quaternary ammonium or cationic protonated amino moieties. The cationic protonated amines can be primary, secondary, or tertiary amines, depending upon the particular species and the selected pH of the composition. Preferably the cationic protonated amines are secondary or tertiary.

The average molecular weight of the cationic polymer is from about 1000 to about 5,000,000 grams/mole and preferably from about 5000 to about 3,000,000 grams/mole. The polymers have a cationic charge density ranging from about 0.2 meq/gm to about 7 meq/gm. The charge density can be measured using the Kjeldahl method. The pH will range from about pH 3 to about pH 9, preferably from about pH 4 to about pH 7.

Any anionic counterions can be used in association with the cationic polymers so long as the counterions do not otherwise unduly impair product performance, stability or aesthetics. Non limiting examples of such counterions include halides (e.g., chlorine, fluorine, bromine, iodine), sulfate and methylsulfate. The cationic nitrogen-containing moiety of the cationic polymer is generally present as a substituent on all or on some of the monomer units thereof. Thus, the cationic polymer for use in the personal care composition includes homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the International Cosmetic Ingredient Dictionary and Handbook, Seventh Edition, (The Cosmetic, Toiletry, and Fragrance Association, Inc., Washington, D.C. (1997)).

Non limiting examples of suitable cationic polymers include copolymers of vinyl monomers having cationic protonated amine or quaternary ammonium functionalities with spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers preferably have from C I to C7 alkyl groups, more preferably from C I to C3 alkyl groups. Other suitable spacer monomers include vinyl esters, vinyl alcohol (made by hydrolysis of polyvinyl acetate), maleic anhydride, propylene glycol, and ethylene glycol. Suitable cationic protonated amino and quaternary ammonium monomers for inclusion in the cationic polymers of the personal care compositions herein, include vinyl compounds substituted with dialkylaminoalkyl acrylate, dialkylaminoalkyl methacrylate, monoalkylaminoalkyl acrylate, monoalkylamino alkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the C1, C2 or C3 alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably CI-C7 hydrocarbyls, more preferably C I-C3 alkyls. Other suitable cationic polymers for use in the personal care composition include copolymers of I-vinyl-2-pyrrolidone and I-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. under the LUVIQUAT tradename (e.g., LUVIQUAT FC 905); copolymers of I-vinyl-2-pyrrolidone and dimethylamino ethyl methacrylate (referred to in the industry by CTFA as Polyquaternium-11), such as those commercially available from ISP Corporation under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from about 3 to about 5 carbon atoms, as described in U.S. Pat. No. 4,009,256. Other suitable cationic polymers for use in the personal care compositions include polysaccharide polymers, such as cationic cellulose derivatives and cationic starch derivatives. Suitable cationic polysaccharide polymers include those which conform to the formula

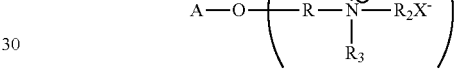

wherein A is an anhydroglucose residual group, such as a starch or cellulose anhydroglucose residual; R is an alkylene, oxyalkylene, polyoxyalkylene, or hydroxyalkylene group, or combination thereof, R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion. Suitable cationic cellulose polymers are those polymers available from Amerchol Corp. in their Polymer JR and LR series of polymers, as salts of hydroxyethyl cellulose reacted with trimethyl ammonium substituted epoxide, referred to in the industry (CTFA) as Polyquaternium 10. Another suitable cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. under the trade name Polymer LM-200. Other suitable cationic polymers include cationic guar gum derivatives, such as guar hydroxypropyltrimonium chloride, specific examples of which include the Jaguar series commercially available from Rhone-Poulenc Incorporated. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581.

The concentration of the cationic polymer component in the personal care composition generally ranges from about 0.02% to about 15%, preferably from about 0.1% to about 5%, and more preferably from about 0.2% to about 2% by weight of the composition. These polymers may be either soluble or crosslinked. The cationic polymers may be used solely or in combination with other cationic polymers. Suitable cationic polymers are further described in US application 2002/0058596 A1 and WO 01/78671.

Preferred cationic polymers are those that form a visible complex, or coacervate, upon addition to a solution of the dye at levels below about 10% by weight, such as Polyquaternium-6 available from Ondeo Nalco, and Polyquaternium-16. In order to determine if a coacervate has been formed, about 10% of a dye in water solution is prepared, and then approximately 10 grams of the solution is placed in a separate vial. The polymer is added to the vial in small amounts and the weight is recorded. The vial is capped and shaken by hand to disperse the polymer with each addition. Observations are recorded after each addition/shaking. The polymer is added up to 20% in the dye solution. Not being limited by theory, the inventors of the present invention have found that if a coacervate is formed when less than 1% of the polymer has been added, the polymer is likely suitable for use in the present invention. This is a preferred method of measuring coacervate formation, but the method can be modified by one skilled in the art by factors including addition of different concentrations, order of addition (i.e. dyes first), or by adding additional ingredients that may be part of the final formulation. The final method of determination of an adequate cationic polymer is that it reduces staining. In order to determine if the staining is reduced, about 0.3 g of product and control are rubbed by finger separately on skin until uniformly distributed. Excess product is removed from the application finger by paper towel or the like. Application finger for the control and test product are compared visually or by color measurement, preferably visually.

The present invention may comprise a safe and effective amount of an anionic polymer. In general, an anionic polymer is any polymer containing anionic groups and/or groups which may be ionized into anionic groups. The anionic polymers are selected from those that contain units comprising carboxylic acids, sulfonic acid, phosphoric acid, salts of carboxylic acid, sulfonic acid, phosphoric acid, and combinations thereof. Additional suitable anionic polymers can be found in the International Cosmetic Ingredient Dictionary ($7^{th}$ ed. 1997). Preferably, the anionic polymers contain carboxylic acids, sulfonic acids, and their salts. Additional suitable anionic polymers may be selected from the group consisting of polyacrylic acid polymers, polyacrylamide polymers, copolymers of acrylic acid, acrylamide, carageenans, and other natural or synthetic polymers (e.g., polystyrene, polybutene, polyurethane, etc.), carboxy functional siloxanes, naturally derived gums, and combinations thereof. Suitable gums include alginates (e.g., propylene glycol alginate), pectins, modified gums, gum arabic, gum acacia, and combinations thereof. Preferred anionic polymers are selected from the group consisting of polyacrylic acid polymers, polyacrylamide polymers, copolymers of acrylic acid, alginates, pectins, and combinations thereof.

The present invention may comprise a safe and effective amount of nonionic polymers. Nonionic polymers are polymers with little or no ionic groups. Suitable nonionic polymers can be selected from polyacrylate, polyacrylamide, cellulose ethers, polymethacrylate, polyethylene, polypropylene, polybutylene, polydecene, polyethyleneoxide, polypropyleneoxide, polybutyleneoxide, polyurethanes, polyurea, copolymers, and combinations thereof.

Amphiphilic polymers are polymers that contain both anionic and cationic groups. For the purposes of this invention, these polymers can be defined by one skilled in the art as either anionic or cationic, depending on the dye or mixture of dyes present in the formula such that they do not adversely affect the performance or aesthetics of the product.

B. Colorant

The composition of the present invention includes a colorant. In general, colorants are those substances that provide color to a personal care product. The purpose of the colorants is to deliver the desirable shade or color that the user is seeking as well as to even out skin tone by covering or hiding tonal imperfections. Such colorants should be physically and chemically compatible with the essential components described herein, or should not otherwise unduly impair product stability, aesthetics or performance.

The concentration of the colorants generally ranges from about 0.001% to about 50%, preferably from about 0.005% to about 20%, more preferably from about 0.01% to about 10%, by weight of the composition. Suitable colorants for use in the composition herein include pigments, dyes, free dyes, and mixtures thereof.

Pigments are defined as colorants that are insoluble in the medium in which they are being used. Thus, pigments do not substantially dissolve or are insoluble in product or usage. Often, pigments are slightly soluble in the product. This soluble portion of the pigment is referred to as free dye. It is the purpose of this invention to reduce the skin staining that results from the presence of dyes and free dyes in cosmetic compositions. Pigments include, but are not limited to, lakes and encapsulated colorants.

Dyes are colorants that are substantially soluble in the medium in which they are being used. The use of dyes is often intended to provide permanent, semi-permanent or durable color for the hair, skin, or nails. Transient dyes do not provide substantial coloring, dyeing, or staining effect. Transient dyes are often used in personal care and cosmetic products. However, if sufficient concentrations of transient dyes are present, skin staining can occur. This staining is usually not durable and can be washed off or easily removed, and the stain will usually fade over time. However, a high concentration of a transient dye can render it non-transient.

Some of the dyes which can be used herein include, but are not limited to, D&C Yellow No. 7, D&C Red No. 36, FD&C Red No. 4, D&C Orange No. 4, D&C Red No. 6, D&C Red No. 34, FD&C Yellow No. 6, D&C Red No. 33, FD&C Yellow No. 5, D&C Brown No. 1, D&C Red No. 17, FD&C Green No. 3, D&C Blue No. 4, D&C Yellow No. 8, D&C Orange No. 5, D&C Red No. 22, D&C Red No. 21, D&C Red No. 28, D&C Orange No. 11, D&C Yellow No. 10, D&C Violet No. 2, Ext. D&C Violet No. 2, D&C Green No. 6, D&C Green No. 5, D&C Red No. 30, D&C Green No. 8, D&C Red No. 7, FD&C Blue No. 1, D&C Red No. 27, D&C Orange No. 10, D&C Red No. 31, FD&C Red No. 40, D&C Yellow No. 11, CI 10020, CI 16185, CI 16255, CI 45430, CI 73015, CI 74160, carmine, and mixtures thereof.

Water soluble dyes, identified by one skilled in the art, are dyes that are substantially soluble in aqueous solutions. For the purposes of this invention, acid dyes are dyes that contain acidic groups, especially sulphonic acid groups. Preferred examples of water soluble acid dyes are D&C Red 33, FD&C Yellow No. 5, D&C Green No. 5, D&C Yellow No. 8, D&C Yellow No. 10.

Colorants that do not have free dye may also be used in conjunction with the pigments above. Some of these useful herein include, but are not limited to, aluminum powder, ultramarines, bismuth oxychloride, chromium oxide green, chromium hydroxide green, iron oxides, ferric ferrocyanide, manganese violet, titanium dioxide, zinc oxide, mica, bronze powder, copper powder, aluminum stearate, calcium stearate, magnesium stearate, zinc stearate, capsanthin/capsorubin, bentonite, barium sulfate, calcium carbonate, calcium sulfate, carbon black, magnesium carbonate, colored silica, and mixtures thereof. Other suitable colorants and pigments may be found in the International Cosmetic Ingredient Dictionary and Handbook, Seventh Edition.

Encapsulation generally involves sequestering dyes or pigments in a solid substrate. These substrates include polymers and other solids such as silica. A variety of encapsulation methods including core-shell are known in the field. Any encapsulation method is useful herein, and non-limiting methods are described in the following patents and applications: U.S. Pat. No. 3,196,079, DE 1913569, JP 73020302, JP 49075738, JP 50049169, U.S. Pat. No. 4,880,617, JP 59076009, JP 59128322, JP 61047410, JP 61083109, JP 61166827, EP 212870, EP 225799, EP 232001, JP 62209011, U.S. Pat. No. 4,756,906, EP 238225, JP 62254833, U.S. Pat. No. 4,665,107, JP 62234541, JP 63060914, WO 03/015910, JP 63171678, JP 63179972, JP 63196505, JP 63202671, EP 306331, JP 1175920, JP 2164439, JP 3034910, U.S. Pat. No. 5,234,711, WO 9106277, JP 3221137, EP 445342, JP 3293028, EP 522916, JP 5339518, WO 9305753, JP 4001118, JP 10059818, WO 9818867, WO 9850002, U.S. Pat. No. 6,060,084, EP 922449, JP 11197494, WO 9943426, and WO 9962974.

C. Optional Ingredients

Aqueous Carrier

The compositions of the present invention may include an aqueous carrier. The level and species of the carrier are selected according to the compatibility with other components and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources containing mineral cations can also be used, depending on the desired characteristic of the product.

Desquamation Actives

A safe and effective amount of a desquamation active may be added to the compositions of the present invention. Non limiting examples can be found in U.S. Pat. No. 5,681,852.

Anti-Acne Actives

Examples of useful anti-acne actives in the present invention include, but are not limited to, the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Antiperspirant Actives

Antiperspirant actives may also be included in the compositions of the present invention. Suitable antiperspirant actives include astringent metallic salts, especially the inorganic and organic salts of aluminum zirconium and zinc, as well as mixtures thereof. Particularly preferred are the aluminum containing and/or zirconium-containing materials or salts, such as aluminum halides, aluminum chlorohydrate, aluminum hydroxyhalides, zirconyl oxyhalides, zirconyl hydroxyhalides, and mixtures thereof.

Anti-Wrinkle Actives/Anti-Atrophy Actives

The compositions of the present invention may contain a safe and effective amount of one or more anti-wrinkle actives or anti-atrophy actives. Non limiting examples include retinoic acid and its derivatives (e.g., cis and trans); retinol; retinyl esters; niacinamide, and derivatives thereof; sulfur-containing D and L amino acids and their derivatives and salts, particularly the N-acetyl derivatives, a preferred example of which is N-acetyl-L-cysteine; thiols, e.g., ethane thiol; terpene alcohols (e.g., farnesol); hydroxy acids, phytic acid, lipoic acid; lysophosphatidic acid, alpha-hydroxy acids (e.g., lactic acid and glycolic acid), beta-hydroxy acids (e.g., salicylic acid), and skin peel agents (e.g., phenol and the like).

Anti-Oxidants/Radical Scavengers

The compositions of the present invention may include a safe and effective amount of an anti-oxidant/radical scavenger. Non limiting examples include tocopherol acetate, other esters of tocopherol, and mixtures thereof. Tocopherol acetate is especially preferred.

Chelators

The compositions of the present invention may contain a safe and effective amount of a chelator or chelating agent. Non limiting examples of chelators useful in compositions of the subject invention are furildioxime, furilmonoxime, and derivatives thereof.

Flavonoids

The compositions of the present invention may contain a safe and effective amount of flavonoid compound. Flavonoids are broadly disclosed in U.S. Pat. Nos. 5,686,082 and 5,686,367.

Anti-Inflammatory Agents

A safe and effective amount of an anti-inflammatory agent may be added to the compositions of the present invention such as steroidal anti-inflammatory agents, including but not limited to hydrocortisone and nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, one may refer to standard texts, including *Anti-inflammatory and Anti-Rheumatic Drugs*, K. D. Rainsford, Vol. I-III, CRC Press, Boca Raton, (1985), and *Anti-inflammatory Agents, Chemistry and Pharmacology*, 1, R. A. Scherrer, et al., Academic Press, New York (1974).

Anti-Cellulite Agents

The compositions of the present invention may contain a safe and effective amount of an anti-cellulite agent. Suitable agents may include, but are not limited to, xanthine compounds (e.g., caffeine, theophylline, theobromine, and aminophylline).

Topical Anesthetics

The compositions of the present invention may contain a safe and effective amount of a topical anesthetic.

Tanning Actives

The compositions of the present invention may contain a safe and effective amount of a tanning active. Non limiting examples include dihydroxy acetone, tyrosine, tyrosine esters such as ethyl tyrosinate and phospho-DOPA.

Skin Lightening Agents

The compositions of the present invention may contain a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Other suitable skin lightening agents are found in PCT Publication No. 95/34280, PCT Application No. 95/07432, PCT Publication No. 95/23780.

Skin Soothing and Skin Healing Actives

A safe and effective amount of a skin soothing or skin healing active may be added to the present composition. Non-limiting examples herein include panthenoic acid derivatives (including panthenol, dexpanthenol, ethyl panthenol), aloe vera, allantoin, bisabolol, and dipotassium glycyrrhizinate.

Antimicrobial and Antifungal Actives

The compositions of the present invention may contain an antimicrobial or antifungal active. Preferred examples of actives useful herein include those selected from salicylic acid, benzoyl peroxide, glycolic acid, lactic acid, acetyl salicylic acid, hydrocortisone, acetominophen, resorcinol, and mixtures thereof.

Sunscreen Actives

Exposure to ultraviolet light can result in excessive scaling and texture changes of the stratum corneum. Therefore, the compositions of the present invention may contain a safe and effective amount of a sunscreen active. As used herein, "sunscreen active" includes both sunscreen agents and physical sunblocks. Suitable sunscreen actives may be organic or inorganic.

A wide variety of conventional organic sunscreen actives are suitable for use herein. Sagarin, et al., at Chapter VIII, pages 189 et seq., of *Cosmetics Science and Technology* (1972), discloses numerous suitable actives. Nonlimiting suitable sunscreen actives include 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, and mixtures thereof.

Particulate Materials

The compositions of the present invention may contain a safe and effective amount of a particulate material, preferably a metallic oxide. These particulates can be coated or uncoated, charged or uncharged. Charged particulate materials are disclosed in U.S. Pat. No. 5,997,887. Particulate materials useful herein include bismuth oxychloride, iron oxide, mica, mica treated with barium sulfate and TiO2, silica, nylon, polyethylene, talc, styrene, polypropylene, ethylene/acrylic acid copolymer, titanium dioxide, iron oxide, bismuth oxychloride, sericite, aluminum oxide, silicone resin, barium sulfate, calcium carbonate, cellulose acetate, polymethyl methacrylate, and mixtures thereof.

One example of a suitable particulate material contains the material available from U.S. Cosmetics (TRONOX TiO2 series, SAT-T CR837, a rutile TiO2). Preferably, particulate materials are present in the composition in levels of from about 0.01% to about 2%, more preferably from about 0.05% to about 1.5%, still more preferably from about 0.1% to about 1%, by weight of the composition.

Conditioning Agents

The compositions of the present invention may contain a safe and effective amount of a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose); hyaluronic acid; lactamide monoethanolamine; acetamide monoethanolamine; panthenol; allantoin; and mixtures thereof. Also useful herein are the propoxylated glycerols described in U.S. Pat. No. 4,976,953.

Also useful are various $C_1$-$C_{30}$ monoesters and polyesters of sugars and related materials. These esters are derived from a sugar or polyol moiety and one or more carboxylic acid moieties.

Preferably, the conditioning agent is selected from urea, guanidine, sucrose polyester, panthenol, dexpanthenol, allantoin, glycerol, and combinations thereof.

Thickening Agents (Including Thickeners, Structuring and Gelling Agents)

The compositions of the present invention may contain a safe and effective amount of one or more thickening agents, preferably from about 0.05% to about 5%, more preferably from about 0.1% to about 4%, and still more preferably from about 0.25% to about 3%, by weight of the composition.

Classes of thickening agents include the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. Nos. 5,087,445, 4,509,949, 2,798,053, and in *CTFA International Cosmetic Ingredient Dictionary*, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10\text{-}30}$ alkyl acrylates with one or more monomers of acrylic acid, methacrylic acid, or one of their short chain (i.e., $C_{1\text{-}4}$ alcohol) esters, wherein the crosslinking agent is an allyl ether of sucrose or pentaerytritol. These copolymers are known as acrylates/$C_{10\text{-}30}$ alkyl acrylate crosspolymers and are commercially available as Carbopol® 1342, Carbopol® 1382, Pemulen TR-1, and Pemulen TR-2, from B.F. Goodrich. Examples of carboxylic acid polymer thickeners useful herein are those selected from carbomers, acrylates/$C_{10}$-$C_{30}$ alkyl acrylate crosspolymers, and mixtures thereof.

b) Crosslinked Polyacrylate Polymers

The compositions of the present invention may contain a safe and effective amount of crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. Nos. 5,100,660, 4,849,484, 4,835,206, 4,628,078, 4,599,379, and EP 228,868.

c) Polyacrylamide Polymers

The compositions of the present invention may contain a safe and effective amount of polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d) Polysaccharides

A wide variety of polysaccharides are useful herein. "Polysaccharides" refer to gelling agents which contain a backbone of repeating sugar (i.e., carbohydrate) units. Examples of polysaccharide gelling agents include those selected from cellulose, carboxymethyl hydroxyethylcellulose, cellulose acetate propionate carboxylate, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol CS Plus from Aqualon Corporation.

Other useful polysaccharides include scleroglucans which are a linear chain of (1-3) linked glucose units with a (1-6) linked glucose every three units, a commercially available example of which is Clearogel™ CS11 from Michel Mercier Products Inc.

e) Gums

Other thickening and gelling agents useful herein include materials which are primarily derived from natural sources. Examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

f) Additional Thickening Agents

Suitable thickening agents can be selected from the group consisting of silicones, waxes, clays, silicas, salts, natural and synthetic esters, fatty alcohols, and mixtures thereof. Non-limiting examples of these structuring or thickening agents are described below.

Suitable silicones include alkyl siloxane gellants, high molecular weight dimethicones (fluids greater than 1000 mPas), and high molecular weight alkyl, hydroxyl, carboxyl, amino, and/or fluoro-substituted dimethicones (fluids greater than 1000 mPas). Preferred silicone gellants are described in U.S. Pat. Nos. 5,654,362 and 5,880,210, and include cyclomethicone and dimethicone crosspolymers (e.g., Dow Corning 9040).

Waxes can be defined as lower-melting organic mixtures or compounds of high molecular weight, solid at room temperature and generally similar in composition to fats and oils except that they contain no glycerides. Some are hydrocarbons, others are esters of fatty acids and alcohols. Suitable waxes may be selected from the group consisting of natural waxes including animal waxes, vegetable waxes, and mineral waxes, and synthetic waxes including petroleum waxes, ethylenic polymers, hydrocarbon waxes (e.g., Fischer-Tropsch waxes), ester waxes, silicone waxes, and mixtures thereof. Synthetic waxes include those disclosed in Warth, *Chemistry and Technology of Waxes*, Part 2, Reinhold Publishing (1956).

Specific examples of waxes include beeswax, lanolin wax, shellac wax, carnauba, candelilla, bayberry, jojoba esters, behenic acid waxes (e.g., glyceryl behenate which is available from Gattifosse as Compritol®), ozokerite, ceresin, paraffin, microcrystalline waxes, polyethylene homopolymers, polymers comprising ethylene oxide or ethylene (e.g., long chained polymers of ethylene oxide combined with a dihydric alcohol, namely polyoxyethylene glycol, such as Carbowax available from Carbide and Carbon Chemicals company; long-chained polymers of ethylene with OH or another stop length grouping at end of chain, including Fischer-Tropsch waxes as disclosed in *Warth*, supra, at pages 465-469 and specifically including Rosswax available from Ross Company and PT-0602 available from Astor Wax Company), $C_{24\text{-}45}$ alkyl methicones, $C_8$ to $C_{50}$ hydrocarbon waxes, alkylated polyvinyl pyrrolidones (e.g., "Ganex" alkylated polyvinylpyrrolidines available from the ISP Company), fatty alcohols from C20 to C60 (e.g., "Unilins", available from Petrolite Corporation), and mixtures thereof.

Water dispersible and oil dispersible clays may be useful to provide structure or thickening. Suitable clays can be selected from montmorillonites, bentonites, hectorites, attapulgites, sepiolites, laponites, silicates and mixtures thereof.

Suitable water dispersible clays include bentonite and hectorite (such as Bentone EW, LT from Rheox); magnesium aluminum silicate (such as Veegum from Vanderbilt Co.); attapulgite (such as Attasorb or Pharamasorb from Engelhard, Inc.); laponite and montmorillonite (such as Gelwhite from ECC America); and mixtures thereof.

Suitable oil dispersible clays include organophilically modified bentonites, hectorites and attapulgites. Specific commercially available examples of these clays include Bentone 34 (Rheox Corp.)—Quaternium-18 Bentonite; Tixogel VP (United Catalysts)—Quaternium-18 Bentonite; Bentone 38 (Rheox Corp.)—Quaternium-18 Hectorite; Bentone SD-3 (Rheox Corp.)—Dihydrogenated Tallow Benzylmonium Hectorite; Bentone 27 (Rheox Corp.)—Stearalkonium Hectorite; Tixogel LG (United Catalysts)—Stearalkonium Bentonite; Claytone 34 (Southern Clay) Quaternium-18 Bentonite; Claytone 40 (Southern Clay) Quaternium-18 Bentonite; Claytone AF (Southern Clay) Stearalkonium Bentonite; Claytone APA (Southern Clay) Stearalkonium Bentonite; Claytone GR (Southern Clay) Quaternium-18/Benzalkonium Bentonite; Claytone HT (Southern Clay) Quaternium-18/

Benzalkonium Bentonite; Claytone PS (Southern Clay) Quaternium-18/Benzalkonium Bentonite; Claytone XL (Southern Clay) Quaternium-18 Bentonite; and Vistrol 1265 (Cimbar)—Organophilic Attapulgite. These organophilic clays can be purchased as pre-dispersed organophilic clay in either an oil or an organic solvent. The materials are in the form of a heavy paste that can be readily dispersed into the formulation. Such materials include Mastergels by Rheox, United Catalysts, and Southern Clay.

Other thickening agents include fumed silicas and alkali metal or ammonium halides. Examples of fumed silicas include Aerosil 200, Aerosil 300, and the alkyl-substituted fumed silicas such as Aerosil R-100, 200, 800, and 900 series of materials, all available from the DeGussa Corporation.

Preferred thickening agents are those that are substantially inert to the distribution of charge through a fluid, e.g., waxes and high molecular weight silicones and hydrocarbons.

Additional Powdered Ingredients

Suitable powders include various organic and inorganic pigments that color the composition or skin. Organic pigments are generally various types including azo, indigoid, triphenylmethane, anthraquinone, and xanthine dyes which are designated as D&C and FD&C blues, browns, greens, oranges, reds, yellows, etc. Inorganic pigments are generally insoluble metallic salts of certified color additives, referred to as lakes or iron oxides. Suitable pigments include those generally recognized as safe, and listed in C.T.F.A. *Cosmetic Ingredient Handbook*, First Edition, Washington D.C. (1988). Specific examples are red iron oxide, yellow iron oxide, black iron oxide, brown iron oxide, ultramarine, FD&C Red, Nos. 2, 5, 6, 7, 10, 11, 12, 13, 30 and 34; FD&C Yellow No. 5, Red 3, 21, 27, 28, and 33 Aluminum Lakes, Yellow 5, 6, and 10 Aluminum Lakes, Orange 5 Aluminum Lake, Blue 1 Aluminum Lake, Red 6 Barium Lake, Red 7 Calcium Lake, and the like.

Other useful powder materials include talc, mica, titanated mica (mica coated with titanium dioxide), iron oxide titanated mica, magnesium carbonate, calcium carbonate, magnesium silicate, silica (including spherical silica, hydrated silica and silica beads), titanium dioxide, zinc oxide, nylon powder, polyethylene powder, ethylene acrylates copolymer powder, methacrylate powder, polystyrene powder, silk powder, crystalline cellulose, starch, bismuth oxychloride, guanine, kaolin, chalk, diatomaceous earth, microsponges, boron nitride and the like. Additional powders useful herein are described in U.S. Pat. No. 5,505,937.

Of the components useful as matte finishing agents, low luster pigment, talc, polyethylene, hydrated silica, kaolin, titanium dioxide, titanated mica and mixtures thereof are preferred.

Micas, boron nitride and ethylene acrylates copolymer (e.g., EA-209 from Kobo) are preferred for imparting optical blurring effects through light diffraction and for improving skin feel, e.g., by providing a lubricious feel. Another particulate material for improving skin feel is SPCAT 12 (a mixture of talc, polyvinylidene copolymer, and isopropyl titanium triisostearate).

Preferred powders for absorbing oil are spherical, nonporous particles, more preferably having a particle size less than 25 microns. Examples of some preferred oil absorbing powders are Coslin C-100 (a spherical oil absorber commercially available from Englehard), Tospearl (spherical silica commercially available Kobo Industries), ethylene acrylates copolymer such as noted above, and SPCAT 12.

The powders may be surface treated with one or more agents, e.g., with lecithin, amino acids, mineral oil, silicone oil, or various other agents, which coat the powder surface, for example, to render the particles hydrophobic or hydrophilic. Such treatment may be preferred to improve ease of formulation and stability.

Materials for Enhancing Wear or Transfer Resistance

One or more materials for imparting wear and/or transfer resistant properties, e.g., via film forming or substantive properties, may be used in the present compositions. Such materials include film forming polymeric materials. While the level of film forming polymeric material may vary, typically the film forming polymeric material is present in levels of from about 0.01% to about 20%, preferably from about 0.5% to about 10% by weight, more preferably from about 1% to about 8% by weight. Preferred polymers form a non-tacky film which is removable with water used with cleansers such as soap.

Examples of suitable film forming polymeric materials include a) sulfopolyester resins, such as AQ sulfopolyester resins, such as AQ29D, AQ35S, AQ38D, AQ38S, AQ48S, and AQ55S (available from Eastman Chemicals);
b) polyvinylacetate/polyvinyl alcohol polymers, such as Vinex resins available from Air Products, including Vinex 2034, Vinex 2144, and Vinex 2019;
c) acrylic resins, including water dispersible acrylic resins available from National Starch under the trade name "Dermacryl", including Dermacryl LT;
d) polyvinylpyrrolidones (PVP), including Luviskol K17, K30 and K90 (available from BASF), water soluble copolymers of PVP, including PVP/VA S-630 and W-735 and PVP/dimethylaminoethylmethacrylate Copolymers such as Copolymer 845 and Copolymer 937 available from ISP, as well as other PVP polymers disclosed by E.S. Barabas in the *Encyclopedia of Polymer Science and Engineering*, 2 Ed., Vol. 17, pp. 198-257;
e) high molecular weight silicones such as dimethicone and organic-substituted dimethicones, especially those with viscosities of greater than about 50,000 mPas;
f) high molecular weight hydrocarbon polymers with viscosities of greater than about 50,000 mPas;
g) organosiloxanes, including organosiloxane resins, fluid diorganopolysiloxane polymers and silicone ester waxes.

Examples of these polymers and cosmetic compositions containing them are found in PCT Publication Nos. WO96/33689, WO97/17058, and U.S. Pat. No. 5,505,937. Additional film forming polymers suitable for use herein include the water-insoluble polymer materials in aqueous emulsion and water soluble film forming polymers described in PCT publication No. WO98/18431. Examples of high molecular weight hydrocarbon polymers with viscosities of greater than about 50,000 mPas include polybutene, polybutene terephthalate, polydecene, polycyclopentadiene, and similar linear and branched high molecular weight hydrocarbons.

Preferred film forming polymers include organosiloxane resins comprising combinations of $R_3SiO_{1/2}$ "M" units, $R_2SiO$ "D" units, $RSiO_{3/2}$ "T" units, $SiO_2$ "Q" units in ratios to each other that satisfy the relationship $R_nSiO_{(4-n)/2}$ where n is a value between 1.0 and 1.50 and R is a methyl group. Note that a small amount, up to 5%, of silanol or alkoxy functionality may also be present in the resin structure as a result of processing. The organosiloxane resins must be solid at about 25° C. and have a molecular weight range of from about 1,000 to about 10,000 grams/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or $R_3SiO_{1/2}$ "M" units and the quadrafunctional or $SiO_2$ "Q" units, otherwise known as "MQ" resins as disclosed in U.S. Pat. No. 5,330,747. In the present invention the ratio of the "M" to "Q" functional units is preferably about 0.7 and the value of n is 1.2. Organosiloxane resins such as these are commercially available such as Wacker 803 and 804 available from Wacker Silicones Corporation of Adrian Mich., and G. E. 1170-002 from the General Electric Company.

Other materials for enhancing wear or transfer resistance include trimethylated silica. Suitable silicas of this type and cosmetic compositions containing them are described in U.S. Pat. No. 5,800.

Emulsifiers

The compositions hereof may contain one or more emulsifiers to enhance the formation and stability of the composition. Compositions of the invention typically comprise from about 0.5% to about 10%, preferably from about 1% to about 5%, more preferably from about 1.5% to about 3% of one or more emulsifiers.

The hydrophilic-lipophilic balance value of the emulsifier (herein referred to as HLB) is chosen so as to optimally lower the interfacial tension between two phases of significantly different surface tension. For a polar-in-non-polar system, HLB ranges are typically from about 4 to about 8. For a non-polar-in-polar system, HLB ranges are typically from about 12 to about 20. HLB factors are described in Wilkinson and Moore, *Harry's Cosmeticology,* 7th Ed. 1982, p. 738. and Schick and Fowkes, Surfactant Science Series, Vol. 2, *Solvent Properties of Surfactant Solutions*, p 607. Exemplary emulsifiers include those disclosed in the C.T.F.A. Cosmetic Ingredient Handbook, 3rd Ed., Cosmetic and Fragrance Assn., Inc., Washington D.C. (1982) pp. 587-592; and Remington's Pharmaceutical Sciences, 15th Ed. 1975, pp. 335-337; and McCutcheon's Volume 1, *Emulsifiers & Detergents,* 1994, North American Edition, pp. 236-239.

Particularly useful emulsifiers for the present compositions include polydiorganosiloxane-polyoxyalkylene copolymers. Such polymers are described in U.S. Pat. No. 4,268,499. Suitable copolymers of this type are known and many are available commercially. A preferred emulsifier of this type is known by its CTFA designation as dimethicone copolyol. Preferred emulsifiers are further disclosed in U.S. Pat. No. 5,143,722.

Another preferred class of emulsifiers are high molecular weight polymeric emulsifiers such as are effective for stabilizing glycol/polyol-in-hydrocarbon systems (e.g., Arlacel P135 commercially available from Unichema).

Co-Solubilizers

The compositions hereof may contain one or more co-solubilizers to enhance the formation and stability of the composition. The co-solubilizer is especially useful to bridge compatibility of two materials which are normally incompatible, resulting in the creation of a single, stable phase. Co-solubilizers may therefore be particularly preferred in the single phase electrostatically sprayable compositions described herein. When used, compositions of the invention typically comprise from about 0.5% to about 10%, preferably from about 1% to about 5%, more preferably from about 1.5% to about 3% co-solubilizer.

Suitable co-solubilizers are best chosen using a solubility parameter scale as is described in "Solubility: Effects in Product, Package, Penetration, and Preservation," by C. D. Vaughan, *Cosmetics and Toiletries*, Vol. 103, Ocober 1988. Based on the solubility parameter of two incompatible materials, a third material with a solubility parameter in between that of the two incompatible materials may sometimes be found which is independently compatible with the two incompatible materials. When all three materials are then combined, they may exhibit the properties of a single stable phase, as could be measured, visually for example, via a light microscope.

Co-solubilizers can be polar fluids, non-polar fluids, polar aprotic solvents, or amphiphilic materials and are chosen from these broad categories to fit the needs of the two incompatible materials to create a single phase.

Particularly useful co-solubilizers include the polydiorganosiloxane-polyoxyalkylene copolymers described, including the polymers described in U.S. Pat. No. 4,268,499, as well as the surfactants disclosed in U.S. Pat. No. 5,143,722. Dimethicone copolyol is preferred.

D. Spectrophotometric Curve

As used herein, both "spectrophotometric curve" and "spectral curve" refer generally to a plotted curve displaying an ordinate value of relative reflectance versus an abscissa value of wavelength of light, typically within the visual range of about 400-700 nm. As used herein, the "first derivative" of the spectrophotometric curve or spectral curve refers generally to a plotted curve displaying the ordinate values of $\Delta\% R/\Delta\lambda$ versus an abscissa value of wavelength of light, typically within the visual range of about 400-700 nm, wherein R is reflectance and $\lambda$ is wavelength. It is generally known that various perceived colors can be compared, particularly by measuring and plotting the reflectance of light across visible wavelengths to produce a spectral curve. Once the spectral curves of the perceived colors are produced, it is then possible to compare the measured curves for any distinguishing color characteristics that are exhibited by the individual colors. Spectral curves can be measured by any number of methods known to those skilled in the art. Particularly noted are the instruments from Data Color International that yield spectral curve in a reflectance mode. Spectrophotometric curves are described in US 2003/0003065 A1. Preferably, the composition of the present invention mimics the spectral curve of skin.

Preferably, a first derivative of the spectrophotometric curve comprises: a) a maximum peak in the region of from about 430 nm to about 520 nm occurs at a wavelength not greater than about 480 nm; b) a maximum peak in the region of from about 420 nm to about 650 nm occurs at a wavelength of from about 570 nm to about 630 nm; and c) a minimum valley in the region of from about 520 nm to about 580 nm has $\Delta\% R/\Delta\lambda$ of less than or equal to about 0.03, wherein R is reflectance and $\lambda$ is wavelength, and wherein the cosmetic composition comprises a mixture of at least two colorants, wherein a first derivative of the spectrophotometric curve of each of the individual colorants does not exhibit (a), (b) and (c).

Associated Methods

Applicants have found that the compositions of the present invention are useful in a variety of applications directed to enhancement of mammalian skin, hair, and nails. The methods of use for the compositions disclosed and claimed herein include, but are not limited to: 1) methods of increasing the substantivity of a cosmetic to skin; 2) methods of moisturizing skin; 3) methods of improving the natural appearance of skin; 4) methods of applying a color cosmetic to skin; 5) methods of preventing, retarding, and/or treating wrinkles; 6) methods of providing UV protection to skin; 7) methods of preventing, retarding, and/or controlling the appearance of oil; 8) methods of modifying the feel and texture of skin; 9) methods of providing even skin tone; 10) methods of preventing, retarding, and/or treating the appearance of spider vessels and varicose veins; 11) methods of masking the appearance of vellus hair on skin; 12) methods of concealing blemishes and/or imperfections in human skin, including acne, age spots, freckles, moles, scars, under eye circles, birth marks, post-inflammatory hyperpigmentation; 13) methods of enhancing or modifying skin color such as lightening, darkening, making more pink, making more yellow, making less dull, making less ashy, making less orange, making more radiant; 14) methods of artificial tanning; 15) methods of concealing vitiligo; 16) methods of concealing damage incurred to the skin as a result of trauma, e.g., cosmetic surgery, burns, stretching of skin, etc.; and 17) methods of concealing wrinkles, fine lines, pores, uneven skin surfaces, etc. Each of the methods discussed herein involve topical application of the claimed compositions to skin.

EXAMPLES

The following are non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

Water In Silicone Foundations

|  | Ex. 1 Wt % | Ex. 2 Wt % | Ex. 3 Wt % |
|---|---|---|---|
| Cyclopentasiloxane | 11.59 | 7.77 | 16.14 |
| TiO2 | 8.25 | 10.00 | 8.25 |
| Propyl Paraben | 0.10 | 0.10 | 0.10 |
| Ethyl Paraben | 0.20 | 0.20 | 0.20 |
| Cyclomethicone and Dimethicone crosspolymer | 44.98 | 45.00 | 45.00 |
| Dimethicone/copolyol crosspolymer | 2.50 | 2.51 | 2.48 |
| Cyclopentasiloxane and Dimethicone copolyol | 2.60 | 2.60 | 2.60 |
| Cetyl PEG/PPG-10/1 Dimethicone | — | — | 1.49 |
| Water | q.s. | q.s. | q.s. |
| Polyquaternium-6 | 1.00 | 1.01 | 1.00 |
| Glycerin | 10.00 | 10.00 | 9.99 |
| Methyl Paraben | 0.10 | 0.10 | 0.10 |
| Disodium EDTA | 0.10 | 0.10 | 0.10 |
| Ethylene Brassylate | 0.20 | 0.20 | 0.20 |
| Capric/caprylic triglyceride | 5.99 | 7.37 | — |
| FD&C Yellow 5 encapsulate | 0.52 | 0.63 | 0.51 |
| D&C Yellow 10 encapsulate | 0.49 | 0.60 | 0.49 |
| Carmine encapsulate | 1.63 | 1.97 | 1.63 |
| D&C Red 33 encapsulate | 0.02 | 0.02 | 0.02 |
| D&C Green 5 encapsulate | 0.48 | 0.58 | 0.48 |
|  | 100% | 100% | 100% |

|  | Ex. 4 | Ex. 5 | Ex. 6 | Ex. 7 |
|---|---|---|---|---|
| Oil Phase |  |  |  |  |
| Emulsifiers | 2.50 | 2.50 | 2.50 | 2.50 |
| Volatile Silicones | 28.00 | 28.00 | 28.00 | 28.00 |
| Non-volatiles | 5.00 | 5.00 | 5.00 | 5.00 |
| Colorants* and Fillers | 17.00 | 17.00 | 15.00 | 15.00 |
| Rheological Additives/Fragrance/Preservatives | 1.00 | 1.00 | 1.00 | 1.00 |
| Aqueous Phase |  |  |  |  |
| Polyquaternium-6** | 1.50 | 1.00 | 2.00 | 1.25 |
| Preservatives | 0.5 | 0.5 | 0.5 | 0.5 |
| Propylene glycol | 5.00 | 5.00 | 5.00 | 5.00 |
| Water | q.s. | q.s. | q.s. | q.s. |

*Colorant contains free dye, e.g. water soluble acid dye.
**Merquat 100 as received - Nalco Chemical Company Foundations may be prepared by dispersing or mixing colorants/pigments in silicone phase using a high speed disperser, mill or other methods known in the art to ensure uniform color and efficient use of colorant. Add remainder of additives with heat if necessary to ensure solid waxes are melted. Combine all aqueous phase ingredients with mixing adding the polymer after other ingredients have been dissolved. Cool phases to room temperature if necessary. Slowly add aqueous phase to silicone phase, mixing with stirrer, homogenizer, or other methods know in the art to form emulsion. Final emulsion properties can be modified or adjusted as would be evident to one skilled in the art.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All documents cited in the Background, Summary of the Invention, and Detailed Description of the Invention are, in relevant part, incorporated herein by reference; the citation of any document is not to be construed as an admission that it is prior art with respect to the present invention.

What is claimed is:

1. A cosmetic composition for changing the appearance of keratinaceous substances comprising: an anionic polymer that includes at least one of a carboxylic acid, a sulfonic acid, a phosphoric acid, and salts of these; a colorant capable of staining said keratinaceous substances, and an aqueous carrier, wherein said polymer mitigates staining of said keratinaceous substances caused by said colorant, and said polymer and said colorant are opposite in charge.

2. The composition of claim 1 wherein said aqueous carrier is water.

3. The composition of claim 1 wherein said colorant is selected from the group consisting of pigments, dyes, encapsulated colorants, lakes, and mixtures thereof.

4. The composition of claim 3 wherein said colorants are transient dyes.

5. The composition of claim 4 wherein said transient dyes are watersoluble dyes.

6. The composition of claim 1 comprising from about 0.02 to about 15 weight percent of said polymer.

7. The composition of claim 1 comprising from about 0.1 to about 5 weight percent of said polymer.

8. The composition of claim 1 comprising from about 0.2 to about 2 weight percent of said polymer.

9. The composition of claim 1 wherein said polymer is capable of forming a coacervate with said colorant.

10. The composition of claim 1 wherein said composition mimics the spectral curve of skin.

11. The composition of claim 1 having a spectrophotometric curve, wherein a first derivative of the spectrophotometric curve comprises: a) a maximum peak in the region of from about 430 nm to about 520 nm occurs at a wavelength not greater than about 480 nm; b) a maximum peak in the region of from about 420 nm to about 650 nm occurs at a wavelength of from about 570 nm to about 630 nm; and c) a minimum valley in the region of from about 520 nm to about 580 nm has $\Delta\% R/\Delta\lambda$ of less than or equal to about 0.03, wherein R is reflectance and $\lambda$ is wavelength, and wherein the cosmetic composition comprises a mixture of at least two colorants, wherein a first derivative of the spectrophotometric curve of each of the individual colorants does not exhibit (a), (b) and (c).

12. A method of mitigating skin staining through a personal care composition comprising: the step of combining a cationic colorant and a polymer; wherein the polymer comprises at least one of a carboxylic acid, a sulfonic acid, a phosphoric acid, and salts of these; and said colorant and said polymer are opposite in charge.

13. The method of claim 12 wherein said colorant is a free dye.

14. The method of claim 13 wherein said free dye is a by-product of an encapsulated dye.

15. The method of claim 13 wherein said free dye is a by-product of a lake.

* * * * *